United States Patent [19]

Tracy et al.

[11] Patent Number: 5,846,926
[45] Date of Patent: Dec. 8, 1998

[54] NONIONIC GEMINI SURFACTANTS WITH THREE HYDROPHILIC HEADS AND TWO LIPOPHILIC TAILS

[75] Inventors: David James Tracy; Ruoxin Li, both of Plainsboro; Jiang Yang, Hightstown, all of N.J.

[73] Assignee: Rhodia Inc., Cranbury, N.J.

[21] Appl. No.: 871,107

[22] Filed: Jun. 9, 1997

[51] Int. Cl.$^6$ .......................... C11D 1/722; C07C 43/11; C07C 49/76; C07C 317/00; C07C 321/00
[52] U.S. Cl. .............. 510/506; 564/85; 568/23; 568/28; 568/48; 568/332; 568/609
[58] Field of Search .................. 568/609, 305, 568/48, 23, 28, 332; 510/506

[56] References Cited

U.S. PATENT DOCUMENTS

| | | | |
|---|---|---|---|
| 2,374,354 | 4/1945 | Kaplan | 260/309.6 |
| 2,524,218 | 10/1950 | Bersworth | 252/117 |
| 2,530,147 | 11/1950 | Bersworth | 260/404.5 |
| 2,776,997 | 1/1957 | Doumani | 260/609 |
| 3,244,724 | 4/1966 | Guttman | 260/309.6 |
| 3,855,156 | 12/1974 | Marumo | 252/547 |
| 3,888,797 | 6/1975 | Marumo | 252/527 |
| 4,892,806 | 1/1990 | Briggs et al. | 430/449 |
| 5,160,450 | 11/1992 | Okahara et al. | 252/174.21 |
| 5,403,922 | 4/1995 | Garelli-Calvet | 536/1.11 |
| 5,488,180 | 1/1996 | Jenkins et al. | 568/609 |
| 5,534,197 | 7/1996 | Scheibel et al. | 510/356 |
| 5,585,516 | 12/1996 | Varadaraj et al. | 562/42 |
| 5,643,864 | 7/1997 | Li et al. | 510/499 |
| 5,656,586 | 8/1997 | Li et al. | 510/535 |

FOREIGN PATENT DOCUMENTS

| | | |
|---|---|---|
| 688781 | 12/1995 | European Pat. Off. . |
| 43 21 022 | 11/1994 | Germany . |
| 48-75821 | 12/1973 | Japan . |
| 60-80848 | 8/1985 | Japan . |

OTHER PUBLICATIONS

Allouch, et.al. Nonionic Amphiphilic Compounds from Aspartic Acid and Glutamic Acids as Structural Mimics of Lecithins. JAOCS 73; No. 1 (1996) 87–95.

Eastoe, et.al. Properties of New Glucamide Surfactants. Langmuir 12 (1996) 2701–2705.

(List continued on next page.)

Primary Examiner—Paul Lieberman
Assistant Examiner—John R. Hardee
Attorney, Agent, or Firm—Craig M. Bell; John Daniel Wood

[57] ABSTRACT

A novel class of nonionic gemini surfactants and methods for their preparation consist of compounds with three hydrophilic heads and two lipophilic tails of the general formula:

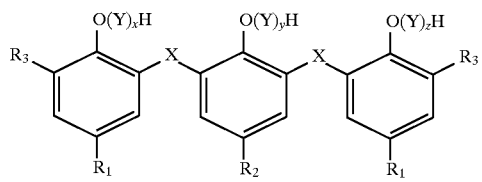

wherein $R_1$ and $R_3$ independently represents a $C_1$ to $C_{22}$ straight or branched chain alkyl, alkylene, aryl or alkylaryl, or hydrogen, with the proviso that both cannot be hydrogen; $R_2$ represents a $C_1$ to $C_5$ straight or branched chain alkyl, alkylene or hydrogen, (Y) represents $$-CH_2\overset{R_4}{\underset{|}{C}}HO-;$$

wherein $R_4$ represents $C_1$ to $C_3$ alkyl or hydrogen and may be the same or different; X represents $-(CH_2)_a-$ wherein a is a whole number of from 1 to 5; $-S-$, $-S-S-$, $-SO_2$, $-(CH_2)_aSO_2(CH_2)_a-$, $-O-$, $-C=O$, or $-CH_2-NR-CH_2-$ wherein R is a $C_1$ to $C_3$ straight or branched chain alkyl, alkylene or hydrogen and x, y, and z are whole numbers of from about 6 to about 300. The surfactants exhibit excellent surface active functionality, low cmc and $pC_{20}$ values and provide superior efficacies when combined with conventional single chain surfactants.

24 Claims, 1 Drawing Sheet

OTHER PUBLICATIONS

Seguer, et.al. Nonionic Amphiphilic Compounds from Lysine as Molecular Mimics of Lecithins. JACOS 73 No. 1 (1996) 79–85.

Zhang, et.al. Novel Polysaccharide Surfactants. The Effect of Hydrophilic and Hydrophobic Chain Length on Surface Active Properties. J. Colloid Interface Sci. 177 (1996) 419–426.

Andre–Barres, et.al. New Double Chain Surfactants Derived from Glucose and Lactose. New J. Chem 19,, No. 4, (1995) 345–347.

Briggs, et.al. Synthesis and Properties of Some Novel Nonionic Polyol Surfactants. J. Chem. Soc. (1995) 379–380.

Eastoe, et.al. Properties of a Dichained Sugar Surfactant. Langmuir 10 (1994) 4429–4433.

Seguer, et.al. New Nonionic Surfactants from Lysine and Their Performance. J. Dispersion Sci. and Tech. 15; No. 5 (1994) 591–610.

Latge, et.al. Synthesis of Long Chain N–Alkyllactamines from Unprotected Lactose: a New Series of Nonionic Surfactants. J. Dispersion Sci. and Tech. 12; No. 3 (1991) 227–237.

Micich, et.al. Wetting Properties of Nonionics from Branched Fatty Amides. JAOCS 65 No. 5 (1988) 820–825.

Hjelmeland, et.al. A New Class of Nonionic Detergents with a Gluconamide Polar Group. Anal.Biochem 130 (1983) 485–490.

Emmerling, et.al. Preparative Methods for the Preparation of Higher Maltoligomers and Their Coupling with Aliphatic Diamines. Starch 33 (1981) 202–208.

M. Rosen: Geminis: A New Generation of Surfactants. Chemtech (Mar. 1993) 30–33.

Menger, et.al. Gemini Surfactants: A New Class of Self Assembling Molecules J. Am. Chem. Soc. 115 (1993) 10083–10090.

Seki, et.al. Characterization of the Complexes of Amphiphilic Polyanions and Double Chain Cationic Surfactants. Macromolecules 25 (1992) 6540–6546.

Menger, et.al. Gemini Surfactants: Synthesis and Properties. J. Am. Chem. Soc. 113 (1991) 1451–1452.

Tschierske, et.al. Novel Thermotrophic and Lyotropic Double Headed Diol–Based Mesogens. J. Chem. Soc. (1990) 1013–1014.

Fuhrhop, et.al. Routes to Functional Vesicle Membranes Without Proteins. Angew. Chem. Intl. Ed. Engl. 23 (1984) 100–113.

Lin, I. Critical Micelle Concentration, Hydrophile Lipophile Balance, Etc. of Ionic Surfactants Containing Two Long Chain Alkyl Groups. Tenside Detergents; 17; No. 3 (1980) 113–123.

Zhu et al. Preparation and Surface Active Properties of Amphipathic Compounds with Two Sulfate Groups and Two Lipophilic Alkyl Chains. JAOCS 67; No. 7 (Jul. 1990) 459–463.

Zhu et al. Preparation and Properties of Glycerol Based Double or Triple Chain Surfactants with Two Hydrophilic Ionic Groups. JAOCS 69; No. 7 (Jul. 1992) 626–632.

Zhu et al. Preparation and Properties of Double or Triple Chain Surfactants with Two Sulfonate Groups. JAOCS; 68; No. 7 (Jul. 1991) 539–543.

Zhu et al. Preparation and Properties of New Surface–Active Amphipathic Compounds with Two Phosphate Groups and Two Long Chain Alkyl Groups. JAOCS; 68; No. 4 (Apr. 1991) 268–271.

NONIONIC GEMINI SURFACTANTS WITH THREE HYDROPHILIC HEADS AND TWO LIPOPHILIC TAILS

This invention relates to an improved class of surfactants useful as emulsifiers and in detergents and personal care products at very low concentrations. The surfactants also exhibit little to no toxicity which makes them useful in a wide variety of applications including personal care, cosmetics, and pharmaceuticals.

Emulsification is an extremely important technology in the chemical arts and it is a process which is used in detergency, emulsion polymerization, cosmetics, food, agrochemicals, paints, paper, the stabilization of crude oil, etc. Emulsifiers function as essential ingredients in personal care and household products; industrial and institutional cleaners including hair shampoos, car washes, carpet shampoo, hand dishwashing liquids, latex foaming compositions, oil recovery compounds; and the like.

In order to form a relatively stable emulsion, an emulsifier is required to adsorb at an oil-water interface to prevent emulsion droplet coalescence. The majority of emulsifiers are synthetic surfactants or natural products with amphiphilic characteristics. Presently, usage levels of surfactants for effective emulsification are usually above 0.1% active based on the total weight of the detergent solution which is the end product comprising the final use composition. For a given emulsifier system, it would be advantageous to use a lower amount of surfactant in order to reduce the cost and amount of surfactant necessary to achieve the desired end result while at the same time creating less waste that is eventually discharged into the environment notwithstanding its ability to improve the performance of final products (e.g., the film forming and water resistance will be improved in latex paints and skin irritation will be reduced for cosmetic products).

While conventional surfactants generally have one hydrophilic group and one hydrophobic group, recently a class of compounds having at least two hydrophobic groups and at least two hydrophilic groups have been introduced. These have become known as "gemini surfactants" in the literature (*Chemtech*, March 1993, pp 30–33), and *J. American Chemical Soc.*, 115, 10083–10090, (1993) and the references cited therein). Other gemini surfactant compounds, that is, compounds having at least two hydrophilic groups and at least two hydrophobic groups are also disclosed in literature but often are not referred to expressly as gemini surfactants.

A number of gemini surfactants are reported in the literature, see for example, Okahara et al., J. Japan Oil Chem. Soc. 37; 746 (Yukagaku) (1989); Zhu et al., JAOCS. 67 No. 7,459 (July 1990); Zhu et al., JAOCS. 68 No. 7, 539 (1991); Menger et al., J. Am. Chem. Soc. 113, 1451 (1991); Masuyama et al., J. Japan Oil Chem. Soc. 41 No. 4, 301 (1992); Zhu et al., JAOCS 69 No. 1, 30 (January 1992); Zhu et al., JAOCS 69 No. 7, 626 (July 1992); Menger et al., J. Am. Chem. Soc. 115 No. 2, 10083 (1993); Rosen, Chem Tech 30 (March 1993); and Gao et al., JAOCS 71 No. 7, 771 (July 1994), all of this literature incorporated herein by reference.

U.S. Pat. No. 5,585,516 to Varadaraj et. al. discloses two tail-two head and two tail-one head surfactants including biphenolic hydrocarbon moieties. Also, gemini surfactants are briefly disclosed in U.S. Pat. No. 2,374,354, to Kaplan; U.S. Pat. Nos. 2,524,218, and 2,530,147 to Bersworth (two hydrophobic tails and three hydrophilic heads); U.S. Pat. No. 3,244,724 to Guttmann; and U.S. Pat. No. 5,160,450 to Okahara, et al., all of which are incorporated herein by reference.

U.S. Pat. No. 5,534,197 to Scheibel teaches a method for the preparation of a nonionic gemini surfactant wherein the hydrophilic head is a sugar or carbohydrate while the hydrophobic head is a long chain alkyl, the two joined by a short alkyl chain. U.S. Pat. Nos. 3,888,797 and 3,855,156, both to Marumo, disclose a number of nonionic gemini surfactant species in which the hydrophobic portion is comprised of a long chain lower alkyl or alkylene while the hydrophilic portion is comprised of an ethoxylate group. U.S. Pat. No. 4,892,806 to Briggs and EP 0,688,781, A1 to Adams also disclose sugar-based hydrophilic heads joined to the hydrophobic counterpart by a short chain carbon bridge. Each moiety would contain a hydrophilic group, e.g., polyoxyethylene, and a hydrophobic group, e.g., an alkyl chain.

A second generation of gemini surfactants has now been discovered comprised of three hydrophilic heads and two lipophilic tails that exhibit even greater surface active properties at very low concentrations as indicated by their extremely low critical micelle concentration (cmc) values, $pC_{20}$ values, Draves wetting values and the like. Moreover, these surfactants, when employed at very low levels, can be mixed with other conventional surfactants and dramatically improve the cleaning and surface tension properties of these surfactants as well.

Zhu, et al. JAOCS 68; No. 7, 539 (1991) teaches the preparation and properties of bis(sulfonate) amphipathic compounds with three long chain alkyl groups. The compounds were prepared by reacting N-acetyldiethanolamine diglycidylethers with long chain fatty alcohols. These triple chain surfactants are asserted to be soluble in water and exhibit superior micelle formation and surface active properties than conventional single chain surfactants.

Zhu, et al. JAOCS, 69; No. 7, 626 (1992) disclose the preparation and properties of glycerol-derived double or triple-chain surfactants with two hydrophilic ionic groups. The ionic groups are comprised of sulfate, sulfonate and carboxylate groups, and the surfactants allegedly exhibit superior surface active properties such as micelle formation and the ability to lower surface tension as opposed to conventional single and even double chain surfactants.

Gao, et al. JAOCS, 71; No. 7, 771 (1994) investigates the dynamic surface tensions of a number of surfactants, some being gemini surfactants with three hydrophobic chains. It is asserted that the apparent diffusion coefficient decreases with an increase in the number of alkyl chains and the resulting bulkiness of the surfactant molecule.

None of the surfactants disclosed in the prior art suggest or disclose the novel class of triple-headed nonionic gemini compounds comprised of three hydrophilic heads and two lipophilic tails as disclosed herein. These not only exhibit extremely low cmc and $pC_{20}$ values, they have excellent surface active functionalities even at very low concentrations. This is reflected in superior detergency and emulsification characteristics as well.

SUMMARY OF THE INVENTION

A novel class of nonionic gemini surfactants and methods for their preparation consist of compounds with three hydrophilic heads and two lipophilic tails of the general formula:

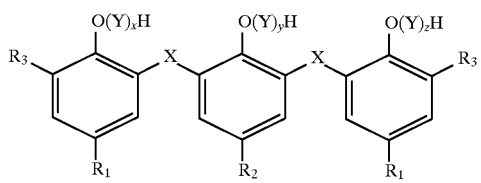

wherein $R_1$ and $R_3$ independently represent a $C_1$ to $C_{22}$ straight or branched chain alkyl, alkylene, aryl or alkylaryl, or hydrogen, with the proviso that both cannot be hydrogen; $R_2$ represents a $C_1$ to $C_5$ straight or branched chain alkyl, alkylene or hydrogen, (Y) represents

wherein $R_4$ represents $C_1$ to $C_3$ alkyl or hydrogen and may or may not be the same or different; X represents —$(CH_2)_a$— wherein a is a whole number of from 1 to 5; —S—, —S—S—, —$SO_2$—, —$(CH_2)_a SO_2(CH_2)_a$——$O$—, —C=O, or —$CH_2$—NR—$CH_2$— wherein R is a $C_1$ to $C_3$ straight or branched chain alkyl, alkylene or hydrogen and x, y, and z are whole numbers of from about 6 to about 300. The surfactants exhibit excellent surface active functionality, low cmc and $pC_{20}$ values and provide superior efficacies when combined with conventional single chain surfactants.

DETAILED DESCRIPTION OF THE INVENTION

Figure 1:
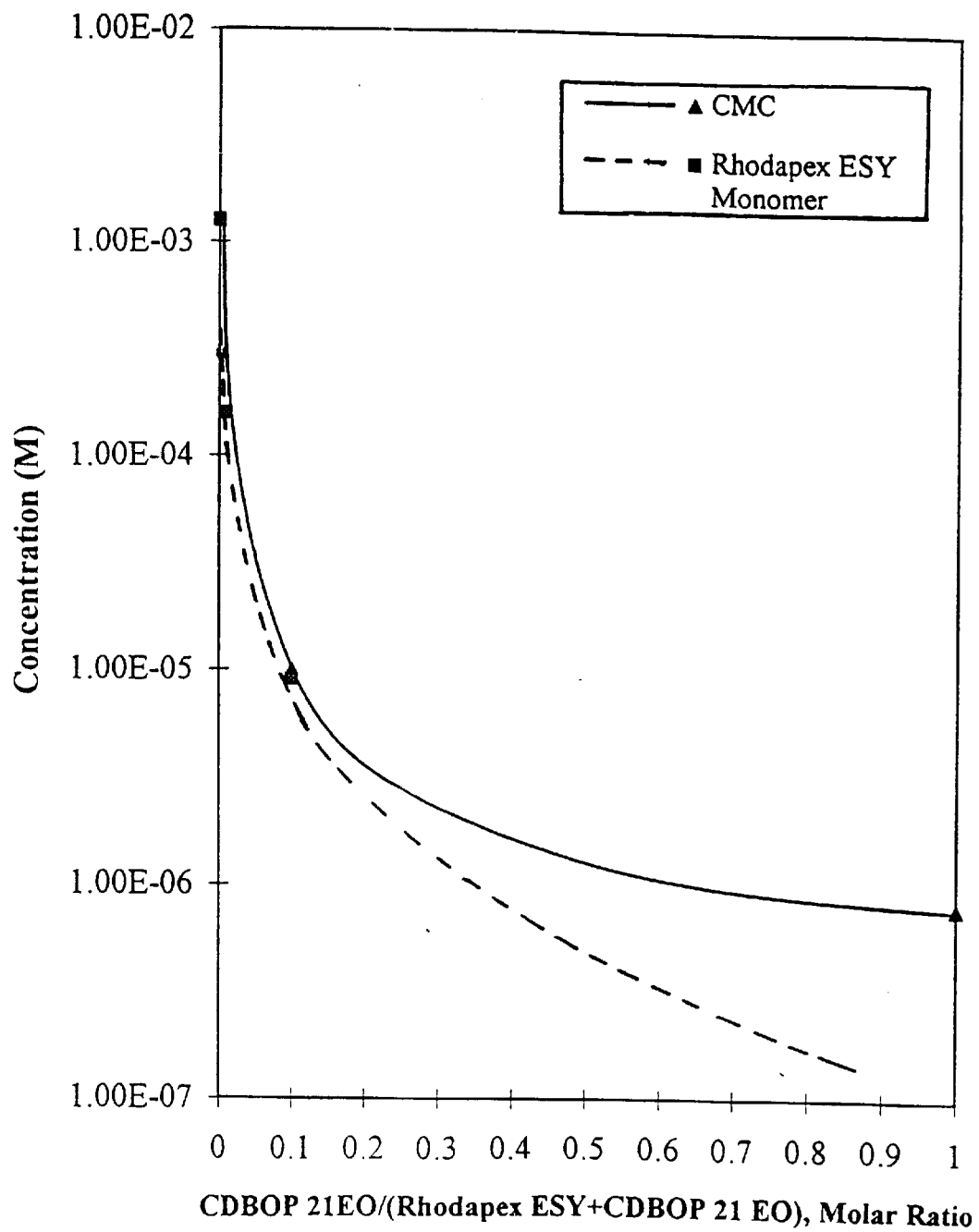

The novel gemini surfactants of the present invention are nonionic alkoxylated bis-alkylphenolic compounds with three hydrophilic heads and two lipophilic (hydrophobic) tails. The novel surfactant compounds are of the general formula:

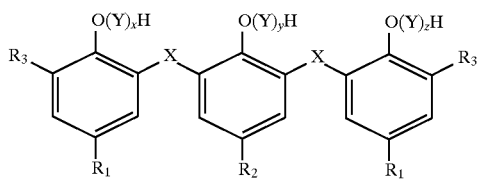

wherein $R_1$ and $R_3$ independently represent a $C_1$ to $C_{22}$ straight or branched chain alkyl, alkylene, aryl or alkylaryl, or hydrogen, with the provisos that both cannot be hydrogen; $R_2$ represents a straight or branched chain $C_1$ to $C_5$ straight or branched chain alkyl, alkylene or hydrogen; (Y) represents

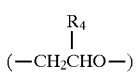

wherein $R_4$ represents a $C_1$ to $C_3$ alkyl or hydrogen which can either be the same or different; X represents —$(CH_2)_a$— where a is a whole number of from 1 to 5; —S—, —S—S—, —$SO_2$—, —$(CH_2)_a SO_2(CH_2)_a$—, —O—, —C=O, or —$CH_2$—NR—$CH_2$— wherein R is a $C_1$ to $C_3$ straight or branched chain alkyl, alkylene or hydrogen; and x, y and z are whole numbers from 6 to 300.

More specifically, the triple hydrophilic headed gemini surfactants of the present invention are ethoxylated 2, 6-dimethylene cresol (bis)octyl phenolic compounds wherein $R_1$ is $C_8H_{17}$, $R_2$ is a methyl group (—$CH_3$), and $R_3$ is hydrogen; i.e. phenol, 2,6 bis[[5-(1,1,3,3, tetramethylbutyl) 2-hydroxyphenyl] methyl] -4-methyl, a tris-phenoxy ethoxylate, which for the purposes of this application will be abbreviated TPE.

The gemini surfactants of the present invention can be prepared using a fairly straight forward coupling reaction in which an alkylphenol or substituted alkylphenol is joined with another like or different alkylphenol or substituted alkylphenol utilizing a coupling reagent. The specific coupling reagent used can vary and will determine the identity of X in the generic formula above. The general reaction scheme for the coupling of an alkylphenol with a bis (hydroxymethyl) alkylphenol may be structurally represented as follows:

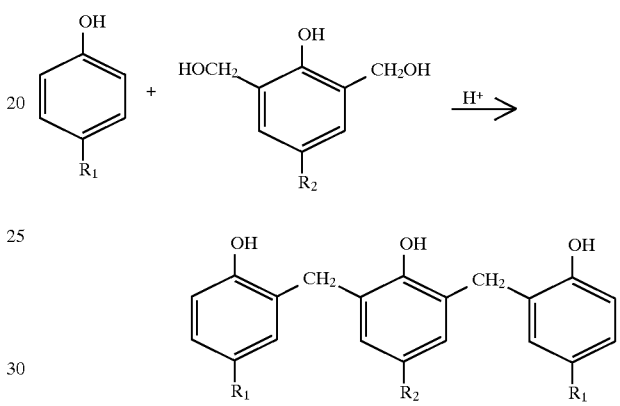

Similarly, a disubstituted phenol can be coupled with an alkylphenol according to the following scheme:

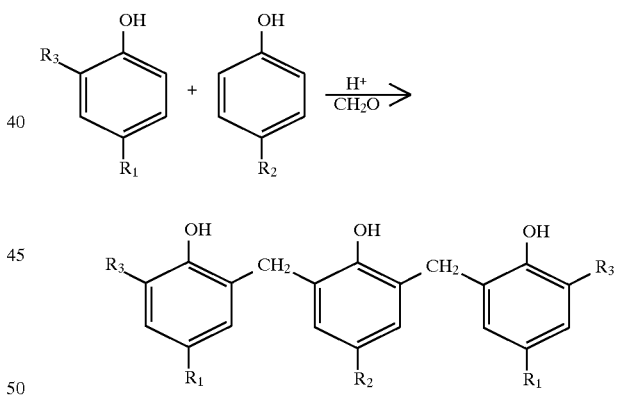

As pointed out above, the methyl (—$CH_2$—) bridging groups between the phenols, shown here as (—$CH_2$), can be varied through the use of different coupling agents and non-substituted alkylphenols. For example, sulphur dichloride can be used in place of formaldehyde to prepare the following:

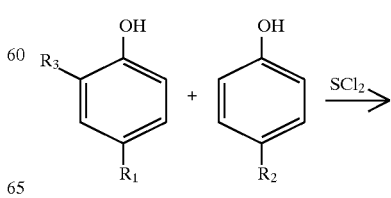

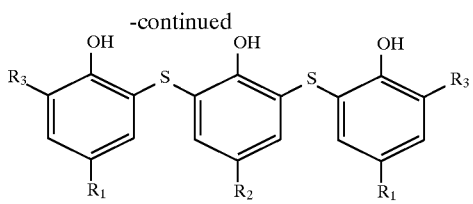

The use of sulphur monochloride ($S_2Cl_2$) in place of the sulphur dichloride yields the same compounds with a double sulphur (—S—S—) bridge.

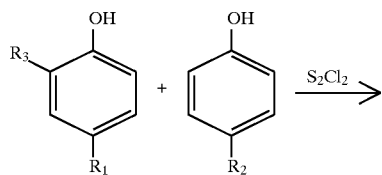

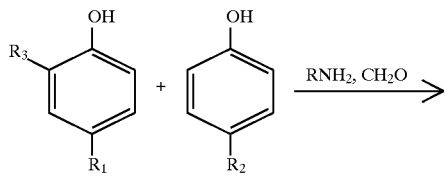

Other reagents can be utilized to prepare a wide variety of gemini compounds with different bridging groups. Suitable acid catalysts for the reaction of aldehydes and ketones with phenolics include acetic acid ($CH_3CO_2H$), propionic acid ($CH_3CH_2CO_2H$), and phosphoric acid ($H_3PO_4$), sulphuric acid ($H_2SO_4$), boron trifluoride ($BF_3$), aluminum chloride ($AlCl_3$), oxalic acid ($CO_2H)_2$ and mixtures thereof.

Other suitable coupling reagents for the condensation reaction between the alkylphenol with a substituted or non-substituted alkylphenol include acetaldehyde ($CH_3CHO$), propionaldehyde ($CH_3CH_2CHO$), acetone ($CH_3COCH_3$), methylamine formaldehyde ($CH_3NH_2$;$HCHO$) and mixtures thereof. Reactions coupling the alkylphenols using these compounds could be represented as follows:

a) Acetaldehyde

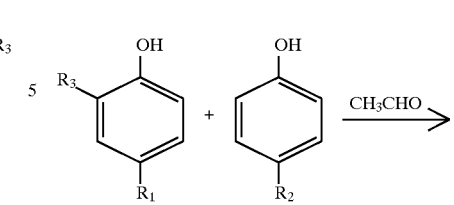

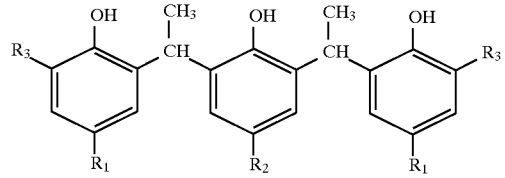

wherein $R_1$, $R_2$, and $R_3$ have been hereinbefore defined.

b) Acetone

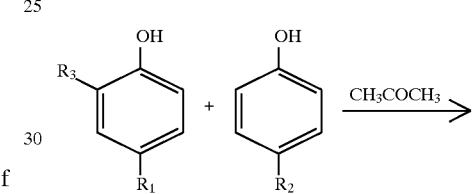

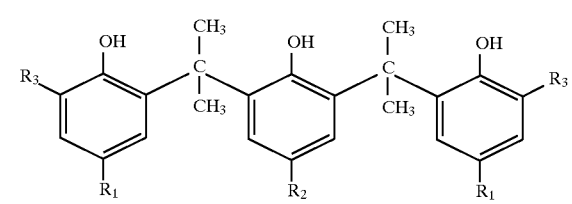

wherein $R_1$, $R_2$ and $R_3$ have been hereinbefore defined.

c) Alkyl amine Formaldehyde

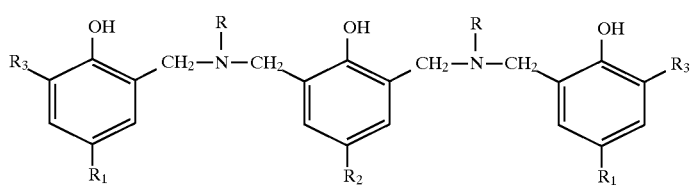

wherein R is a $C_1$ to $C_3$ straight or branched-chain alkyl, alkylene or hydrogen and $R_1$, $R_2$ and $R_3$ have been hereinbefore defined.

d) Hydroxyethylsulfone

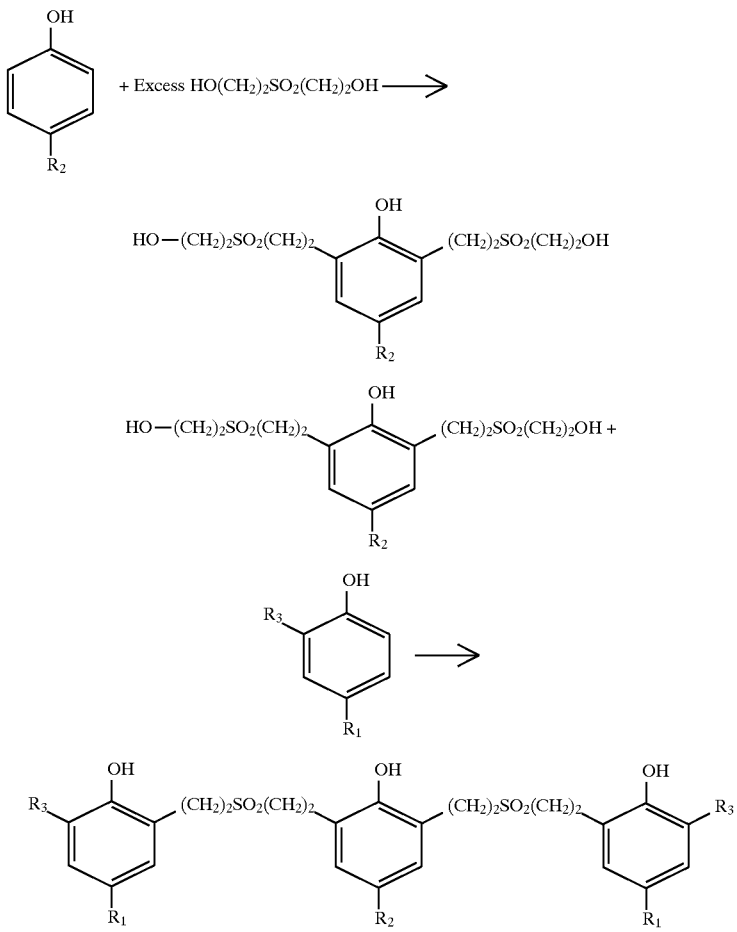

As briefly mentioned earlier, the bridging X group of the generic formula set forth at the beginning of this section is essentially determined by the degree of substitution on the alkylphenolic reactants and preferably, X independently represents a methylene group; $R_1$ represents a $C_5$ to $C_{22}$ straight or branched-chain alkyl, alkylene, aryl or alkylaryl, and $R_2$ and $R_3$ represent a $C_1$ to $C_5$ straight or branched chain alkyl, alkylene, or hydrogen.

Once the coupling reaction has occurred, preferably the compounds are ethoxylated at the OH⁻ site so as to produce the triple lipophilic tail. Ethoxylation may be carried out by adding ethylene oxide slowly to the reaction mixture under elevated temperature and pressure. In the alternative, the compounds may also be propoxylated or butoxylated using propylene oxide or butylene oxide, respectively. The compounds can also be simultaneously ethoxylated/propoxylated or ethoxylatedbutoxylated, thereby yielding mixed or blocked copolymers.

The novel gemini surfactants of the present invention can be used above or in combination as a blend with other known surfactants.

It has also been unexpectedly found that blends of the compounds of the invention with certain conventional well known anionic, nonionic, cationic and amphoteric surfactants provide results beyond that expected and therefore synergistic that can be demonstrated in relation to critical micelle concentration and surface tension reducing ability.

Examples of the nonionic surfactants used herein include fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, an alkylpyrrolidone, glucamides, alkylpolyglucosides, mono- and dialkanol amides, a polyoxyethylene alcohol mono or diamides and alkyl amine oxides. Examples of the anionic surfactants used herein include fatty acid soaps, ether carboxylic acids and salts thereof, alkane sulfonate salts, α-olefin sulfonate salts, sulfonate salts of higher fatty acid esters, higher alcohol sulfate ester salts, fatty alcohol ether sulfates salts, higher alcohol phosphate ester salts, fatty alcohol ether phosphate ester salts, condensates of higher fatty acids and amino acids, and collagen hydrolysate derivatives. Examples of the cationic surfactants used herein include alkyltrimethylammonium salts, dialkyldimethylammonium salts, alkyldimethylbenzylammonium salts, benzethonium chloride, and acylamino acid type cationic surfactants. Examples of the amphoteric surfactants used herein include amino acid, betaine, sultaine, phosphobetaines, imidazoline type amphoteric surfactants, soybean phospholipid, and yolk lecithin.

In addition to the foregoing surfactants, any of commonly used auxiliary additives may be added to the surfactants of the invention or blends thereof with other surfactants as disclosed herein. Such auxiliary additives may be added to the surfactants of the invention on use. Such auxiliary additives may be suitably chosen for a desired composition and generally include inorganic salts such as Glauber salt and common salt, builders, humectants, solubilizing agents, UV absorbers, softeners, chelating agents, and viscosity modifiers.

The anionic surfactants of the invention are extremely mild and non-irritating to both eyes and skin. They also exhibit enhanced wetting speed, greater surface tension reduction, high foaming and foam stabilization properties, low toxicity, and excellent compatibility with other anionic, ionic, and nonionic surfactants. The products of the invention are stable over a wide pH range and are biodegradable. These properties make these surfactants adaptable for use in products ranging from cosmetics to industrial applications and are usable wherever anionic surfactants have found use. These products are particularly useful for non-irritating shampoos, including baby shampoos, body shampoos including bubble baths, bar soaps, bath gels, hair conditioning gels, lotions, skin creams and lotions, male up removal creams and lotions, liquid detergents, dish detergents and other washing and cosmetic products that contact the skin. The surfactants of the invention can also find use as hard surface cleaners including cars, dishes, toilets, floors, carpets, and the like; laundry detergents and soaps, metal working aids and the like.

The following examples are provided to better describe specific ways in which one skilled in the art can prepare the surfactant compounds of the present invention. They are for illustrative purposes only and it is recognized that there are many alterations or changes that can be made with respect to the starting materials, process parameters, and other reactants that are not contemplated thereby. It is to be understood that to the extent any such changes do not materially alter the process or final products, they are deemed as falling within the spirit and scope of the invention as later recited in the claims.

EXAMPLE 1

Preparation of 2,6,bis [[5-(1,1,3,3 - tetramethylbutyl)-2-hydroxyphenyl]methyl]-4-methylphenol ethoxylate (TPE).

A.) Preparation of 2,6, bis-[[5-(1,1,3,3-tetramethylbutyl)-2-hydroxyphenyl] methyl]-4-methylphenol.

(4-tert-Octyl) phenol (430 gm) and 2,6-dihydroxymethyl-p-cresol (80 gm) were melted and stirred at 150° C. in nitrogen. Acetic acid (16 ml) was added drop-wise to the solution. The reaction was stirred for 16 hours. Water generated during the reaction was collected by the Dean-Stark azeotropic method. The reaction was stopped by distilling out excess of octylphenol at 180° C. under vacuum. This process took about an hour. The yield of the crude product was about 100% based on starting material, 2,6-dihydroxymethyl-p-cresol. Pure product can be obtained by washing the crude product with hexane two times. The final product was a white powder. Both $^1$H-NMR and $^{13}$C-NMR results agreed with the structure of the product.

B.) Preparation of TPE 2,6,bis-[[5-(1,1,3,3-tetramethylbutyl)-2-hydroxyphenyl] methyl]-4-methylphenol (202.5 gm) was melted at 150° C in a 2 gallon autoclave under nitrogen. Potassium hydroxide (3.24 gm, 45% water solution) was added to the autoclave. The mixture was stirred for 30 minutes at 140° C. under vacuum to remove trace water. After the air inside the autoclave was replaced with nitrogen, the autoclave was heated to 160°–170° C. Ethylene oxide (470 gm) was added slowly under this temperature range. The pressure of EO inside the reactor was maintained under 53 psig. After a few hours of constant pressure and the remainder of the amount of ethylene oxide was added, the autoclave was cooled to 120° C. and vacuum stripped with a slight nitrogen for 20 minutes. Finally, after cooling, the pH of the final product was adjusted to 7 by adding acetic acid. NMR results indicated about 21 moles of ethylene oxide had been reacted.

The chemical structure of ethoxylated 2,6-dimethylene cresol bisoctylphenol was determined to be the following:

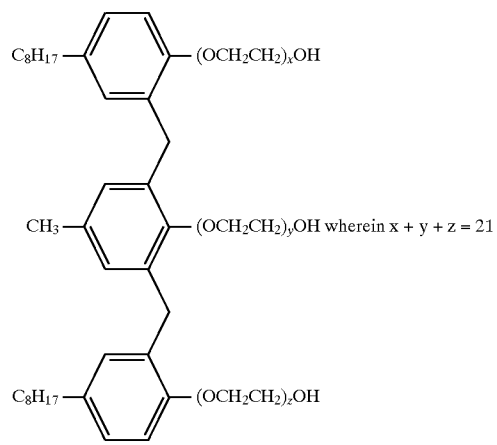

The molecular weight of the compound is 1441.9.

EXAMPLE 2

Preparation of Ethoxylated Phenol, 2,6-bis[[3,5-di(1,1-dimethylpropyl)-2-hydroxyphenyl]thio]-4-methyl A). Preparation of Phenol, 2,6-bis-[[3,5-di(1,1-dimethylpropyl)-2-hydroxyphenyl]thio]-4-methyl:

To 234 gm (1.0 mole) 2,4-di(1,1-dimethylpropyl)phenol and 54 gm (0.5 mole) ρ-cresol was added 102 gm (1.0 mole) sulfur dichloride slowly over a three (3) hour period at 55° C. to 60° C. The reaction mixture was stirred rapidly and sparged with nitrogen to remove any hydrogen chloride. The hydrogen chloride was bubbled into a sodium hydroxide solution. After the addition was complete, the reaction was held for an additional 2 hours at 60° C.

The reaction was cooled and discharged. Residual chloride analysis showed none remaining and the NMR confirmed the major component was the structure below.

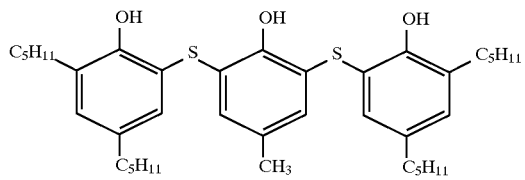

B.) Ethoxylation

To 636 gm (1.0 mole) of adduct prepared in part A was added 4400 g (100 mole) ethylene oxide. The reaction was run at 150° C. under 50 psig in the presence of 2 gm potassium hydroxide. The product, after neutralization, was analyzed by NMR which indicated a 100 mole ethoxylate. The product possessed excellent foaming properties.

EXAMPLE 3

Preparation of Ethoxylated 2,6-bis-[[3,5-di(1,1-dimethylpropyl)-2-hydroxyphenyl]dithio]-4-methylphenol A.) Preparation of 2,6-bis-[[3,5-di(1,1-dimethylpropyl)-2-hydroxyphenyl]dithio]-4-methylphenol:

Sulfur monochloride (135 gm) was added slowly to 234 gm (1.0 mole) 2,4-di (1,1-dimethylpropyl)phenol and 54.0 g (0.5 mole) p-cresol over a 3 hour period at 50° C. to 60° C. The reaction mixture was stirred rapidly with a nitrogen sparge to remove any hydrogen chloride. The hydrogen chloride was trapped in an aqueous solution of sodium hydroxide. After the addition was complete, the reaction was stirred for 3 hours at 60° C. with sparging to complete the reaction. The reaction was cooled and discharged. Analysis by NMR is consistent with the expected structure below:

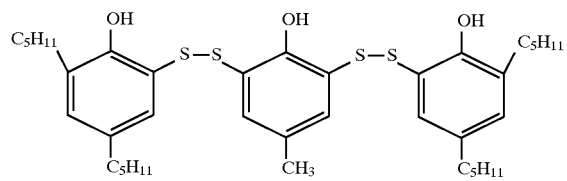

B.) Ethoxylation

To 700 g (1 mole) of adduct prepared in part A and 2 g of potassium hydroxide was added at 150° .C and 50 psig 2200 g (50 mole) of ethylene oxide. The product, after neutralization, was analyzed by NMR and confirmed the structure. The product possessed good foaming properties.

EXAMPLE 4

The surface activity of a blend of the TPE prepared in example 1, together with sodium laurylether sulfate was determined as a function of critical micelle concentration (cmc) values and the monomer concentration of the sodium laurylether sulfate. The critical micelle concentration of the gemini trimeric nonionic surfactant by itself is extremely low, and is $7.9 \times 10^{-7}$M (~0.001 wt %). The surface tension of the surfactant at the critical micelle concentration is 31 dynes/cm at 25° C. Mixtures of the surfactant with the sodium laurylether sulfate in molar ratios of 1/99 and 10/90, respectively, significantly decreased the critical micelle concentration of the non-gemini as shown in the graph of FIG. 1, below. The cmc was reduced 10~100 times and the monomer concentration of the sodium laurylether sulfate was also significantly reduced. Hence, the trimeric gemini is highly surface active even at very low concentrations.

What we claim is:

1. A surfactant composition comprising compounds of the formula:

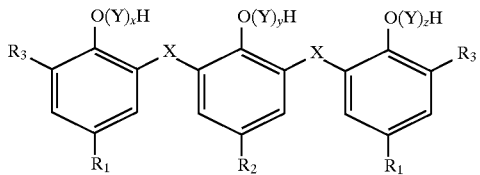

wherein $R_1$ and $R_3$ independently represent a $C_1$ to $C_{22}$ straight or branched chain alkyl, alkenyl, aryl or alkylaryl, or hydrogen, with the proviso that both cannot be hydrogen; $R_2$ represents a $CH_3$ or hydrogen, Y represents

wherein $R_4$ is a $C_1$ to $C_3$ alkyl or hydrogen and may be the same or different, X represents —$(CH_2)_a$—, —S—, —S—S—, —$SO_2$—, $(CH_2)_aSO_2(CH_2)_a$—, —O—, —C=O or —$CH_2$—NR—$CH_2$—wherein R is a $C_1$ to $C_5$ alkyl, alkenyl or hydrogen, a is a whole integer of from 1 to about 5 and x, y and z are whole numbers from about 6 to about 300.

2. The surfactant composition of claim 1 comprising compounds of the formula:

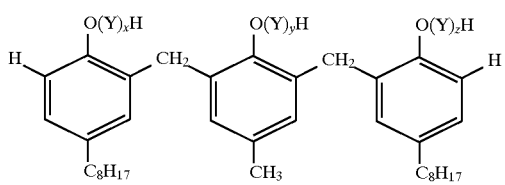

wherein (Y) x, y and z have been hereinbefore defined.

3. The surfactant composition of claim 1 comprising compounds of the formula:

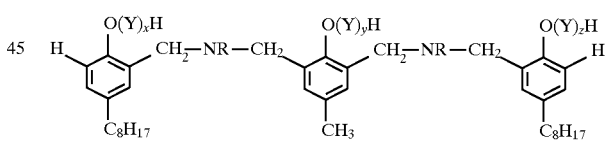

wherein R, (Y), x, y and z have been hereinbefore defined.

4. The surfactant composition of claim 1 comprising compounds of the formula:

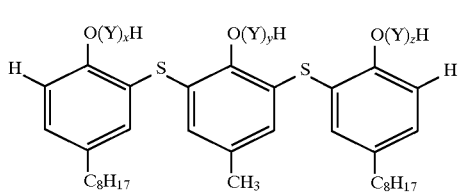

wherein (Y), x, y and z have been hereinbefore defined.

5. The surfactant composition of claim 1 comprising compounds of the formula:

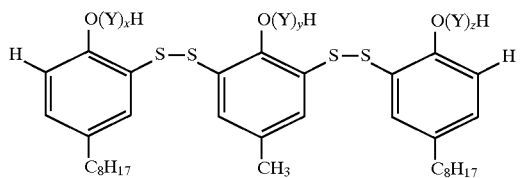

wherein (Y), x, y and z have been hereinbefore defined.

6. The surfactant compositions of claim 1 comprising compounds of the formula:

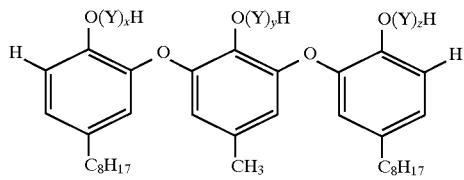

wherein (Y), x, y and z have been hereinbefore defined.

7. The surfactant compositions of claim 1 comprising compounds of the formula:

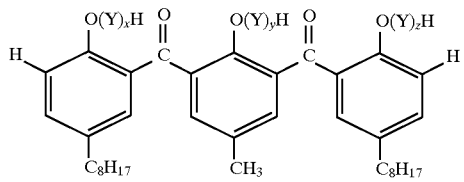

wherein (Y), x, y and z have been hereinbefore defined.

8. The surfactant compositions of claim 1 comprising compounds of the formula:

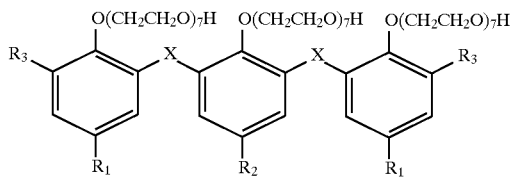

wherein $R_1$, $R_2$, $R_3$ and X have been hereinbefore defined.

9. The surfactant compositions of claim 1 comprising compounds of the formula:

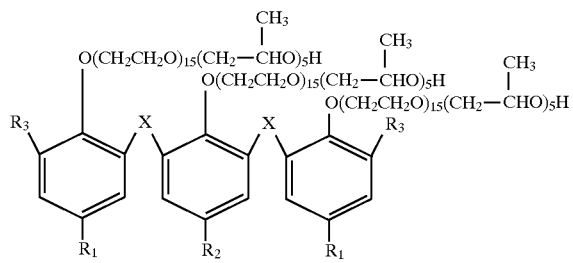

wherein $R_1$, $R_2$, $R_3$ and X have been hereinbefore defined.

10. A surfactant blend comprising the compounds of claim 1 and one or more additional compounds selected from the group consisting of anionic surfactants, nonionic surfactants, cationic surfactants, amphoteric surfactants, and mixtures thereof.

11. A surfactant blend comprising the compounds of claim 2 and one or more additional compounds selected from the group consisting of anionic surfactants, nonionic surfactants, cationic surfactants, amphoteric surfactants, and mixtures thereof.

12. A surfactant blend comprising the compounds of claim 3 and one or more additional compounds selected from the group consisting of anionic surfactants, nonionic surfactants, cationic surfactants, amphoteric surfactants, and mixtures thereof.

13. A surfactant blend comprising the compounds of claim 4 and one or more additional compounds selected from the group consisting of anionic surfactants, nonionic surfactants, cationic surfactants, amphoteric surfactants, and mixtures thereof.

14. A surfactant blend comprising the compounds of claim 5 and one or more additional compounds selected from the group consisting of anionic surfactants, nonionic surfactants, cationic surfactants, amphoteric surfactants, and mixtures thereof.

15. A surfactant blend comprising the compounds of claim 6 and one or more additional compounds selected from the group consisting of anionic surfactants, nonionic surfactants, cationic surfactants, amphoteric surfactants, and mixtures thereof.

16. A surfactant blend comprising the compounds of claim 7 and one or more additional compounds selected from the group consisting of anionic surfactants, nonionic surfactants, cationic surfactants, amphoteric surfactants, and mixtures thereof.

17. The blend of surfactants of claim 10, wherein said nonionic surfactant is selected from the group consisting of fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxethylene lanolin alcohols, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oils or hardened castor oil derivatives, polyoxyethylene lanolin derivatives, polyoxethylene fatty acid amides, polyoxyethylene alkyl amines, alkyl pyrrolidones, glucamides, alkyl polyglucosides, mono- or dialkanol amides, mono- or diamides, polyoxyethylene alcohols, alkylamine oxides and mixtures thereof.

18. The blend of surfactants of claim 10, wherein said anionic surfactant is selected from the group consisting of fatty acid soaps, ether carboxylic acids and the salts thereof, alkane sulfonate salts, α-olefin sulfonate salts, the sulfonate salts of a higher fatty acid ester, higher alcohol sulfate ester salts, fatty alcohol ether sulfate salts, higher alcohol phosphate ester salts, fatty alcohol ether phosphate ester salts, condensates of higher fatty acids and amino acids, collagen hydrolysate derivatives and mixtures thereof.

19. The blend of surfactants of claim 10, wherein said cationic surfactant is selected from the group consisting of alkyltrimethylammonium salts, dialkyldimethylammonium, alkyldimethylbenzylammonium salts, benzethonium chlorides, acylamino acid-type cationic surfactants and mixtures thereof.

20. The blend of surfactants of claim 10, wherein said amphoteric surfactant is selected from the group consisting of an amino acids, betaines, sultaines, phosphobetaines, imidazoline-type amphoteric surfactants, soybean phospholipids, yolk lecithins and mixtures thereof.

21. The surfactant of claim 10 further comprising an auxiliary additive selected from the group consisting of inorganic salts, builders, humectants, solubilizing agents, UV absorbers, chelating agents, viscosity modifiers and mixtures thereof.

22. A cleaning composition comprising an aqueous solution having a cleaningly effective amount of the composition of claim 21 dissolved therein.

23. The cleaning composition of claim 22, wherein the solution is selected from the group consisting of hair shampoos, baby shampoos, body shampoos, bubble baths, bar soaps, bath gels, hair conditioning gels, skin creams and lotions, skin contacting cosmetics, make-up removal creams and lotions, liquid detergents, dish detergents, liquid soaps, bleach activators, bleach stabilizers.

24. The cleaning composition of claim 23, wherein the solution is selected from the group consisting of hard surface cleaners, emulsion polymerization activators, laundry and dish detergents, liquid and bar soaps, carpet cleaners, lubricants, metal cleaners and textile processing aids.

* * * * *